United States Patent [19]

Miller et al.

[11] 4,177,813

[45] Dec. 11, 1979

[54] VESSEL OCCLUDER

[75] Inventors: Curtis H Miller, Burnsville; Robert A. Arp, Eden Prairie, both of Minn.; Howard F. Carpenter, South Easton, Mass.

[73] Assignee: Med General, Inc., Minneapolis, Minn.

[21] Appl. No.: 868,032

[22] Filed: Jan. 9, 1978

[51] Int. Cl.$^2$ .............................................. A61B 17/12
[52] U.S. Cl. .................................... 128/326; 172/346
[58] Field of Search .............. 128/325, 326, 327, 347, 128/346; 251/7, 9, 5

[56] References Cited

U.S. PATENT DOCUMENTS

| | | | |
|---|---|---|---|
| 454,327 | 6/1891 | Brown | 128/326 |
| 1,532,299 | 4/1925 | Braecklein | 128/327 |
| 2,847,014 | 8/1958 | Cohen | 128/327 |
| 2,856,933 | 10/1958 | Hildebrand | 128/305 |
| 3,507,270 | 4/1970 | Ferrier | 128/2.05 F |
| 3,533,410 | 10/1970 | Shannon | 128/326 |
| 3,665,926 | 5/1972 | Flores | 128/326 |
| 3,786,816 | 1/1974 | Wolvek | 128/346 |
| 3,877,434 | 4/1975 | Ferguson | 128/327 |
| 3,892,241 | 7/1975 | Leveen | 128/325 |

*Primary Examiner*—Richard J. Johnson
*Attorney, Agent, or Firm*—Orrin M. Haugen; Thomas J. Nikolai

[57] ABSTRACT

A disposable vascular tourniquet for controlling the constriction of a blood vessel during surgery. The vessel occluder comprises a flexible tubular sheath having a clamping structure disposed at its proximal end. The clamping structure is a unitary molded plastic part which has a tubular base portion adapted to be inserted into the proximal end of the flexible sheath and projecting from this base portion are bifurcated fingers, one of which includes a transversely extending latch portion which is adapted to mate with a recess on the other finger. A retractor or snare having a hook at one end and a ring-type handle at the other end may be inserted between the fingers of the clamp when in its unlatched condition and through the tubular base of the clamp and the sheath so as to extend outwardly from the distal end of the sheath. A cord may be looped around a vessel to be constricted and the ends of the loop are captured in the hook of the retractor. When the retractor is drawn outward from the sheath, the ends of the loop pass between the fingers of the clamp such that when the fingers are pinched together and latched, axial movement of the cord with respect to the tubular sheath is prevented.

9 Claims, 7 Drawing Figures

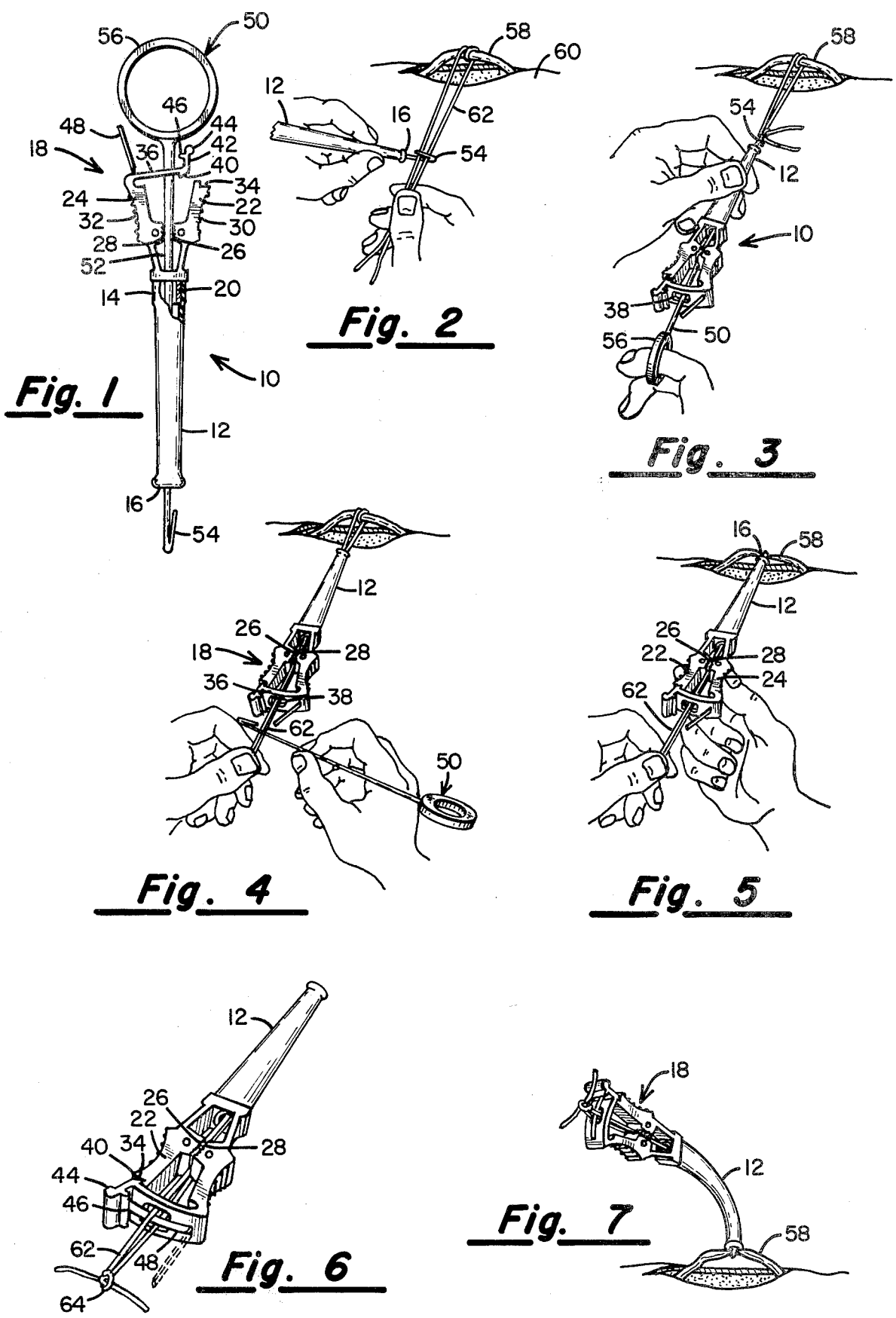

VESSEL OCCLUDER

BACKGROUND OF THE INVENTION

I. Field of the Invention

This invention relates generally to vessel occluding devices used during surgical procedures and more specifically to the design of a vessel occluder having an improved clamping structure for maintaining constant pressure on the blood vessel being constricted.

II. Description of the Prior Art

Many different types of vessel occluders are well known in the art. In general, they include a flexible rubber tubular sheath having a separate retractor which can be passed completely through the sheath. The retractor normally has a hook at its distal end and a handle at its proximal end. A flexible tape or cord is looped around the blood vessel to be constricted and the ends of the cord are snared in the hook of the retractor. When the retractor is withdrawn from the proximal end of the flexible sheath, the ends of the cord are also drawn through the sheath. The loop around the blood vessel may then be drawn tight such that the vessel is compressed and occluded against the distal end of the sheath.

Prior art vessel occluders also employ a suitable clamping arrangement for maintaining the cord taut. Typical prior art clamping structures are disclosed in the Wolvek U.S. Pat. No. 3,786,816 and the Ferguson et al U.S. Pat. No. 3,877,434. In the Wolvek arrangement, the flexible sheath is provided with an outwardly projecting pedestal on which the base of a generally U-shaped metal spring element rests. A notch is provided in the base which is adapted to cooperate with one of the legs of the U-shaped spring. When this leg is inserted into the notch, the side walls of the flexible sheath are compressed against the tape or cord to prevent axial movement thereof.

In the Ferguson arrangement a simple plug is used at the proximal end of the sheath to maintain the desired tension in the vessel occluding cord. A significant drawback to the Ferguson et al approach is the fact that it is generally a two-handed operation to effect a release of the cord so that blood can be made to flow through the previously constricted vessel. That is, one hand must be used to hold the sheath while the other hand is used to remove the plug.

The present invention is considered to be a significant improvement over the structure disclosed in the aforementioned prior art patents. Specifically, vessel occluders made in accordance with the teachings of the present invention offer the advantage of low cost manufacture and ease of use during surgical procedures. The clamping arrangement of the present invention may be released with only one hand and, accordingly, the surgeon has his other hand free to perform simultaneous manipulations.

SUMMARY OF THE INVENTION

The vessel occluder of the present invention comprises an elongated, flexible, tubular sheath having a proximal and a distal end. Disposed in the proximal end of the tubular sheath is a clamp member which has a tubular base portion and integrally formed resilient bifurcated fingers extending from this base portion. One of the fingers is provided with an integrally formed clasp segment which is adapted to engage the other finger for releasably pinching these fingers together.

The system further includes an elongated retractor which may be inserted through the unclasped fingers of the clamp member and through the lumen of the sheath so as to extend beyond the distal end thereof. The retractor has a handle at its proximal end and a hook at its distal end. The hook may be used to snare the ends of a cord which has been passed around a vessel to be constricted and when the retractor is drawn outward from the proximal end of the sheath, the ends of the cord pass between the now open fingers of the clamp. At this point, the retractor member is discarded and when the fingers of the clamp are squeezed together the cord is tightly held between the fingers and the clasp segment latches. To unlatch the clamp and release the tension on the cord, a simple flick of the finger is all that is needed. The clamp member is preferably molded from a suitable plastic which can be accomplished at a very modest cost.

OBJECTS

It is accordingly a principal object of the present invention to provide an improved vessel occluder for use during surgical procedures.

Another object of the invention is to provide a vessel occluder having a new and improved clamp arrangement for maintaining a vessel occluding cord in a taut condition with respect to a blood vessel.

Still another object of the invention is to provide an improved clamp arrangement for a vessel occluder which is easy to manipulate from an open to a closed condition or vice versa, with only one hand.

These and other objects and advantages of the invention will become apparent upon a reading of the following detailed description of the preferred embodiment when considered in conjunction with the accompanying drawings in which like numerals in the several views refer to corresponding parts.

DESCRIPTION OF THE DRAWINGS

FIG. 1 is a side elevation of the vessel occluder with the retractor in position ready for use; and FIGS. 2 through 7 illustrate the sequence and mode of use of the invention.

DESCRIPTION OF THE PREFERRED EMBODIMENT

With reference to FIG. 1, the vessel occluder of the present invention is indicated generally by numeral 10. It includes a flexible tubular sheath 12 of a predetermined length. The tube 12 is preferably formed from rubber or the like, but alternative materials may also be used. The tubular sheath 12 has a proximal end 14 and a distal end 16. Disposed in the proximal end of the sheath 12 is an integrally formed clamping structure indicated generally by numeral 18. The clamping member 18 includes a tubular base portion 20 having an outside diameter slightly larger than the inside diameter of the sheath 12 such that the flexible sheath is stretched about the tubular base portion 20 to firmly hold the clamp member 18 in place.

When viewed as in FIG. 1, the base portion 20 has a set of bifurcated fingers, including fingers 22 and 24, projecting 20 upwardly and outwardly therefrom. Each of the fingers has an inwardly extending projection, as at 26 and 28, the opposed faces of which are serrated. In use, these projections comprise the jaws of the clamp. Upward from the projections 26 and 28, each of the fingers 22 and 24 include a concave outer surface which is also serrated as at 30 and 32. The radius of curvature of these concave side surfaces is such as to conform to the thumb and forefinger of the surgeon.

Formed in the top surface of the finger 22 is a V-shaped notch 34. Integrally formed at the top of the bifurcated finger 24 is a clasp segment 36 which extends in a generally transverse direction with respect to the longitudinal axis of the sheath 12. The clasp segment 36 has an aperture 38 formed therethrough as can best be seen in FIG. 3. Generally located near the end of the clasp 36 is a V-shaped projection or barb 40 which is adapted to cooperate with the V-shaped notch 34 formed in the finger 22.

Also integrally formed proximate the end of the clasp segment 36 is an upwardly extending web 42 which terminates in a generally cylindrically shaped extension 44. Also integrally formed on the web 42 is a horizontally extending rib 46 which is spaced apart from the upper surface of the clasp segment 36 by a predetermined distance. There is also provided an integrally formed security bar which is attached at one end to the upper surface of the clasp segment 36 proximate its connection to the finger 24. The length and thickness of this bar 48 is such that it may be bent from the position illustrated in FIG. 1 so that its free end abuts the underside of the rib 46.

The vessel occluder 10 also includes a removable and disposable retractor member indicated generally by numeral 50. The retractor includes an elongated rod 52 having a hook 54 at its distal end and a handle in the form of a finger ring 56 at its proximal end. The length of the rod 52 is such that when it is inserted through the aperture 38 formed through the clasp 36, it may extend downward between the jaw segments 26 and 28, through the tubular base portion 20 and through the tubular sheath 12 so that the hook 54 extends beyond the distal end 16 of the sheath 12. The retractor member 50 may also be molded from plastic at a modest cost.

Now that the construction of the preferred embodiment has been described in detail, consideration will be given to the manner in which it may be utilized during a surgical procedure. In this regard, reference will be made to the several views of FIGS. 2 through 7 which are intended to depict the sequence as well as the various operating features of the invention.

As is indicated in FIG. 2, a blood vessel 58 has been dissected away from the surrounding tissue 60 and a cord or tape 62 has been wrapped around the exposed vessel. The surgeon then snares the free ends of the cord into the hook 54 of the retractor which is extending from the distal end 16 of the flexible rubber sheath 12.

With reference to FIG. 3, the surgeon next with one hand, withdraws the retractor 50 by exerting force on the handle 56 and with the other hand he slides the vessel occluder assembly 10 towards the vessel 58.

With reference to FIG. 4, when the ends of the cord 62 extend beyond the clamp 18, the surgeon removes and discards the retractor 50. As is shown in FIG. 4, the ends of the cord 62 pass between the now-open jaws 26 and 28 and through the aperture 38 formed in the clasp segment 36.

Now, with reference to FIG. 5, the surgeon next gently pulls on the ends of the cord 62 such that the vessel 58 is constricted or pinched against the distal end 16 of the sheath 12. While holding the cord taut, the surgeon next applies a compressive force to the bifurcated fingers 22 and 24 in the area of the concave serrated surfaces thereof. This force closes the jaws 26 and 28 about the cord and firmly grips the cord to prevent longitudinal movement of the cord with respect to the sheath 12. As the compressive force is applied to the fingers, these fingers move towards one another until the point is reached where the barb 40 of the clasp 36 engages the V-shaped notch 34 formed in the upper end surface of the finger 22. Once the barb mates with the notch, the surgeon may let go of the assembly and the fingers will be restrained from assuming their normal released position by virtue of the latch arrangement described.

During surgical procedures, it is common practice to periodically release the tourniquet so that fresh blood may flow to thereby prevent damage to an organ caused by a prolonged lack of blood supply. To prevent the ends of the cord from going into the lumen of the sheath 12 when the clamp is released, a knot as at 64 may be tied near the ends of the cord 62 and the security bar 48 is bent from the phantom line position illustrated in FIG. 6 so that its end passes through the loop of the cord and engages the underside of the rib 46. Thus, when the clamp is released, the security bar 48 will prevent the vessel occluder from being moved to a position wherein the cord 62 would be lost inside the tubular sheath 12.

To effect release of the clamp, a simple flick of the surgeon's thumb nail against the cylindrical projection 44 will be sufficient to lift the clasp to a point where the barb 40 no longer engages the notch 34. The resilient finger 22 will then spread outwardly to release the engagement of the jaw projections 26 and 28 from the cord 62.

FIG. 7 is included to show the manner in which the flexible sheath 12 may be bent so that the vessel occluder is out of the way during the surgical procedure. It also illustrates the shape and configuration of the clamp member 18.

The only materials resting in contact with the vessel 58 and adjacent parts of the patient's body are the soft textile cord and the soft flexible rubber sheath 12 so that trauma and the danger of possible damage to delicate body parts are minimized. The vessel occluder of the present invention is so simple and inexpensive in its construction that it may be considered to be a disposable unit. However, if desired, the device may be sterilized and reused.

While this invention has been described with particular reference to the construction shown in the drawings, it is to be understood that such is not to be construed as imparting limitations upon the invention, which is best defined by the following claims.

What is claimed is:
1. A vessel occluder comprising:
(a) an elongated tubular sheath having proximal and distal ends;
(b) a clamp member having a tubular base portion adapted to be fitted into said proximal end of said tubular sheath and having integrally formed resilient bifurcated fingers extending from said base portion, one of said fingers terminating in an integrally formed, transversely extending clasp segment having an aperture therethrough, said clasp segment being adapted to engage the other of said fingers for releasably pinching said fingers together; and
(c) an elongated retractor adapted to extend through said aperture in said clasp segment, said tubular base portion and the lumen of said sheath and beyond both ends thereof, said retractor having a handle at its proximal end and a hook at its distal end adapted to snare the ends of a cord or the like looped about a body vessel and draw said ends through the lumen of the sheath, between said bifurcated fingers and through said aperture in said clasp segment, the arrangement being such that when said clasp segment engages the other of said fingers, said cord is restrained from axial movement with respect to said sheath.

2. In a vessel occluder of the type including an elongated tubular sheath having distal and proximal ends and a retractor having a handle at one end and a hook at its other end adapted to be inserted through the lumen of said sheath for drawing the ends of a looped cord through the lumen of said sheath upon withdrawal of said retractor from said sheath, means for releasably securing said loop against axial movement relative to said sheath comprising:

(a) a clamp member having a tubular base portion adapted to be inserted into the proximal end of said sheath and having integrally formed bifurcated fingers extending outwardly from said base portion, one of said fingers having an integrally formed transversely extending latch adapted to releasably engage the other of said fingers to maintain said fingers in a pinched relationship with respect to the ends of said loop only when said latch and said other of said fingers are engaged.

3. The clamp as in claim 2 and further including:

(a) first and second integrally formed projections extending inwardly from each of said bifurcated fingers, said projections defining clamping jaws therebetween.

4. Apparatus as in claim 3 wherein opposed faces of said projections include a serrated surface.

5. Apparatus as in claim 2 wherein said latch includes an aperture therethrough generally aligned with said tubular end portion and of a size to allow said retractor to pass through said aperture.

6. The device as in claim 5 and further including a flexible pin fixedly attached at one end to said latch and oriented to extend across said aperture and releasably secure to said latch.

7. Apparatus as in claim 6 wherein the end of said latch includes an integrally formed tip extending at an oblique angle out of the plane of said latch to define a human finger engaging abutment.

8. Apparatus as in claim 2 wherein each of said fingers includes a concave arcuate portion on the outer surfaces thereof dimensioned to generally conform to the thumb and forefinger of a human and wherein said concave arcuate portions are serrated.

9. The device as in claim 2 wherein said other finger includes a V-shaped notch proximate the free end thereof and said latch includes a V-shaped projection on its undersurface, proximate its free end adapted to cooperate with said V-shaped notch in said other finger.

* * * * *